(12) United States Patent
Marban et al.

(10) Patent No.: US 6,586,241 B1
(45) Date of Patent: *Jul. 1, 2003

(54) METHODS TO IDENTIFY COMPOUNDS AFFECTING MITOCHONDRIA

(75) Inventors: Eduardo Marban, Lutherville, MD (US); Brian O'Rourke, Sparks, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/684,730

(22) Filed: Oct. 6, 2000

Related U.S. Application Data

(63) Continuation of application No. 09/060,774, filed on Apr. 15, 1998, now Pat. No. 6,183,948.

(51) Int. Cl.[7] .................................................. C12N 5/00
(52) U.S. Cl. ............................ 435/325; 435/4; 435/29; 435/404
(58) Field of Search .............................. 435/4, 29, 325, 435/404

(56) References Cited

U.S. PATENT DOCUMENTS

| | | |
|---|---|---|
| 4,273,869 A | 6/1981 | Shapiro |
| 4,808,517 A | 2/1989 | Blondin et al. |
| 5,686,261 A | 11/1997 | Zhang et al. |
| 5,888,498 A | 3/1999 | Davis et al. |
| 6,183,948 B1 * | 2/2001 | Marban et al. |

OTHER PUBLICATIONS

K. Esumi, et al., *Am. J. Physiol.*,260:H1743–H1752 (1991).
J. Eng, et al., *Biopys. J.*, 55:621–630 (1989).
W. Kunz, *FEBS Lett.* 3272, 195:92–96, (1986).
B. Chance, et al., *J. Bio. Chem.*, 254:4764–4771 (1979).
W. Kunz, et al., *Biochem. Med. Metab. Biol.*, 50:103–110 (1993).
L. Rossini, et al., *Pharmacological Research*, 23:349–365 (1991).
B. Chance, et al., *Am. J. Physiol.* 223:207–218 (1972).
G. Hajnoczky, et al., *Cell*, 82: 415–424 (1995).
W. Halangk, et al., *Biochim. Biophys. Acta.*, 1056:273–278 (1991).
W. Kunz, et al., *Anal. Biochem.*, 216:322–327 (1994).
R. Scholtz, et al., *J. Bio. Chem.*, 244:2317–2324 (1969).
H. Franke, et al., *Int. J. Biochem.*, 12:269–275 (1980).
B. Chance, et al., *FEBS Lett.*, 26:315–319 (1972).
B. Sato, et al., *Biochim. Biophys. Acta.*, 1268:20–26 (1995).
I. Hassinen, et al., *Biochem. Biophys. Res. Commun.*, 31:895:900 (1968).
M. Erecinska, et al., *Biochem. Biophys. Res. Commun*, 41:386–392 (1970).
T. Galeotti, et al., *Arch. Biochem. Biophys.*, 131:306–309 (1969).
K. Ozawa, et al., *Biochim. Biophys. Acta.*, 1138: 350–352 (1992).
B. O'Rourke, et al., *Science*, 265:962–966 (1994).
K. Garlid, et al., *Circ. Res.*, 81:1072–1082 (1997).
Y. Liu, et al., *Circulation*, (in press Dec. 8, 1997).
B. O'Rourke, et al., *Science*, 265:962–966 (1994).

* cited by examiner

*Primary Examiner*—Leon B. Lankford, Jr.
(74) *Attorney, Agent, or Firm*—Peter F. Corless; Edwards & Angell, LLP

(57) ABSTRACT

The present invention relates to methods for identifying a compound capable of modulating mitochondrial function, comprising contacting a eukaryotic cell with one or more candidate compounds, and detecting a change in the mitochondrial redox state of the cell. The methods further relates to such methods wherein endogenous fluorescence of the cell mitochondria is indicative of a change of redox state.

3 Claims, 6 Drawing Sheets

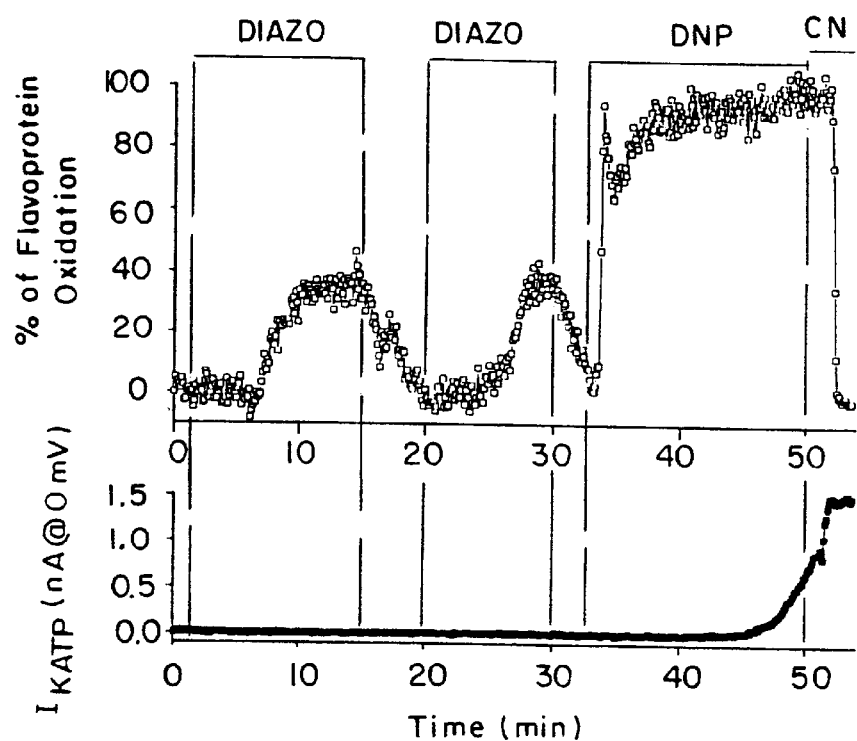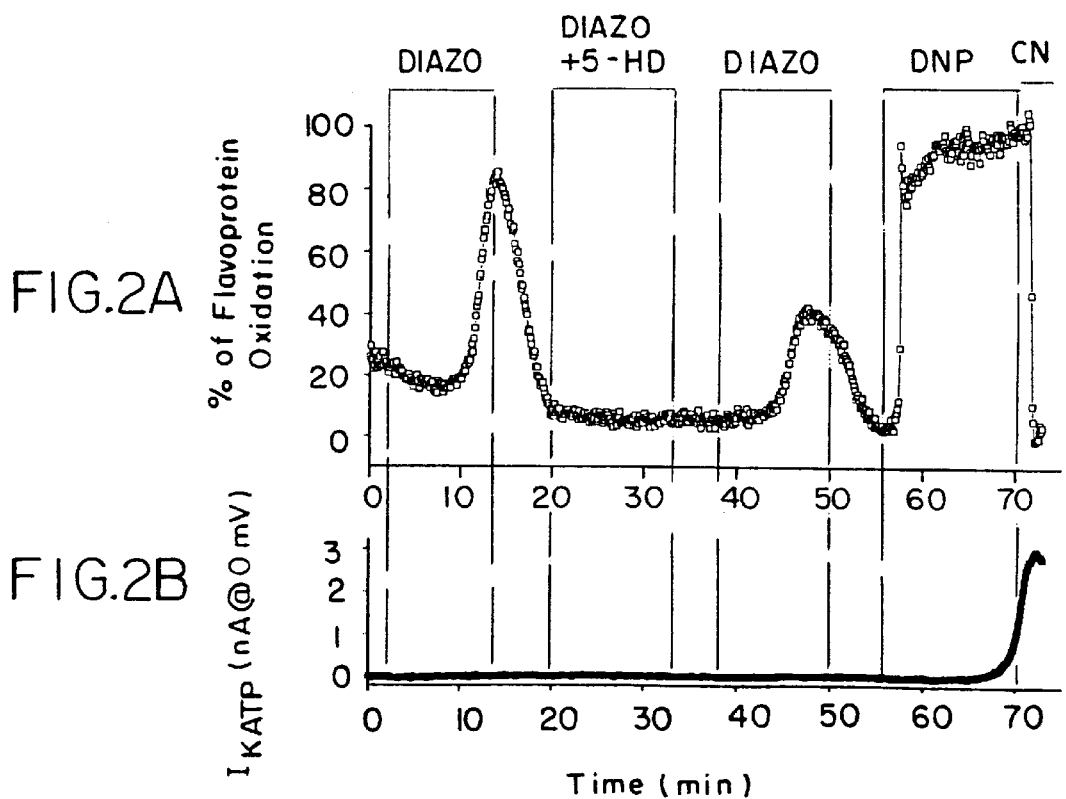

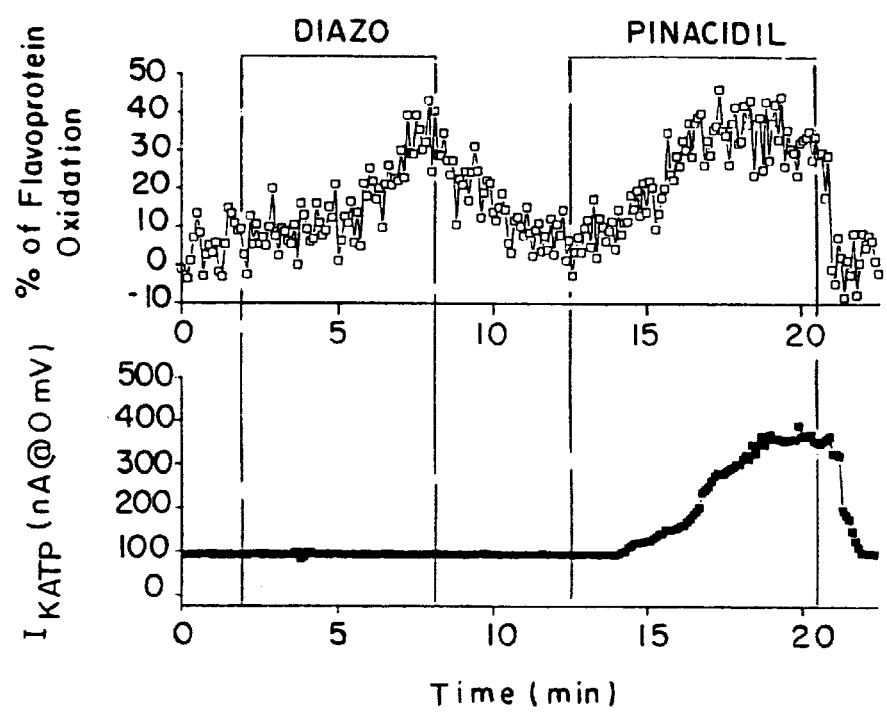

METHODS TO IDENTIFY COMPOUNDS AFFECTING MITOCHONDRIA

CROSS-REFERENCE TO RELATED APPLICATION

The present application is a continuation of U.S. Ser. No. 09/060,774 filed on Apr. 15, 1998 (now U.S. Pat. No. 6,183,948). The disclosure of said U.S. Pat. No. 6,183,948 is incorporated herein by reference.

FIELD OF THE INVENTION

In one aspect, the present invention relates to methods for screening for compounds that modulate mitochondrial function by affecting mitochondrial redox potential. Methods of the invention also can be used to test for mitochondrial fitness.

BACKGROUND OF THE INVENTION

Nearly every cell of the body contains organelles called mitochondria which produce most of the energy used by the body. Certain cells with high metabolic rates, such as heart muscle cells, may contain thousands of mitochondria.

Energy derived from the utilization of substrates is required in order to maintain the non-equilibrium state necessary to carry out the basic functions of the cell (e.g. contraction, secretion, electrical propagation, ion pumping, cell division). There are three major steps involved in cellular energy production. First, large food molecules are broken down into smaller units. Polysaccharides are converted to simple sugars, fat is converted to fatty acids and proteins are converted to amino acids. Second, multiple pathways convert these three different molecules into a common precursor, acetyl CoA, for further oxidation by the mitochondria. Third, the Krebs cycle (a.k.a. the citric acid or tricarboxylic acid cycle) and oxidative phosphorylation convert acetyl CoA into ATP, the energy storage molecule directly utilized by the energy consuming reactions in the cell.

Mitochondrial substrate oxidation is a multi-step process that includes a series of reactions which transfer electrons from the initial substrate to nicotinamide adenine dinucleotide (NAD+) to produce NADH which is then reoxidized by passing electrons through the electron transport chain to the ultimate electron acceptor oxygen. In the process of electron transfer, protons (H+) are pumped out of the mitochondrial matrix (an intracellular aqueous compartment bounded by the inner and outer mitochondrial membranes between it and the cell's cytoplasm) across the mitochondrial inner membrane (IMM) resulting in the establishment of a proton gradient. This proton concentration gradient, together with the large membrane voltage generated by the active charge movement across the IMM, provide the driving force for proton movement back into the matrix (the protonmotive force) which will be utilized by a specific IMM protein (the mitochondrial ATP synthase) to convert ADP (adenosine diphosphate) to ATP (adenosine triphosphate). ATP thus produced is transported out of the mitochondria and is available to perform the work required by the cell.

The relative impermeability of the IMM to ion leak and the presence of energy conserving pumps and exchangers in the membrane allows for the efficient utilization of the protonmotive force for cellular energy production rather than expending it for reestablishing the IMM gradient. Despite this requirement for maintaining a high resistance membrane, the IMM contains a number of energy dissipating high conductance pathways for ion and/or solute movement. The physiological role of some of these pathways is apparent, for example, the pyruvate transporter is required to import substrate into the matrix for oxidative phosphorylation; however, in other cases, the physiological importance of IMM ion conducting pathways is still unknown. A well known example is the mitochondrial megachannel (MMC) or permeability transition pore (PTP). When activated, this large non-selective channel rapidly de-energizes the mitochondrion and has been implicated in several pathophysiological states. Other known high conductance pathways include the calcium uniport, the mitochondrial inner membrane anion channel, the mitochondrial uncoupling protein of brown fat mitochondria, and the mitochondrial ATP-sensitive potassium channel. A number of electrogenic (e.g., the adenine nucleotide transporter, the glutamate-aspartate transporter, the Na—Ca exchanger), proton-compensated electroneutral (e.g., the glutamate, pyruvate, and malate-citrate transporters) and electroneutral (e.g., the malate-phosphate, malate-ketoglutarate, carnitine, ornithine, and neutral amino acid transporters) are also present in the IMM and may influence the mitochondrial energy state. Although some of these channels and transporters have been well studied in isolated mitochondria, for lack of a useful index of mitochondrial activity in intact cells, much less is known about their regulation or sensitivity to pharmacological agents in intact cells.

The mitochondria are essential for efficiently providing ATP for carrying out the myriad functions of the cell, particularly in tissues with a high energy demand, such as muscle and brain. Consequently, defects in mitochondrial energy metabolism are usually associated with significant functional deficits or death. The pathophysiologies related to mitochondrial dysfunction can be either primary or secondary. In primary mitochondrial diseases, a genetic defect (either inborn or acquired) in a mitochondrial protein may lead to the incorrect assembly or catalytic activity of the protein, thus disrupting or impairing the entire biochemical pathway. Secondary mitochondrial disorders may arise from the accumulation of toxic products within the cell (including oxygen free radicals), the accumulation of inhibitory metabolites, or lack of cofactors required for mitochondrial metabolism.

Mitochondrial cytopathies of differing origin often lead to similar clinical symptoms. Commonly the disorders are first expressed in the most metabolically active tissues. They may present as muscle weakness and fatigue, mild muscle ache, or severe (and sometimes lethal) lactic acidosis during exercise. In many cases, these muscle deficiencies are also associated with central nervous system disorders, referred to as mitochondrial encephalomyopathies (e.g, KSS, Kearnes-Sayre syndrome; MERRF, myoclonus epilepsy with ragged red fibres; MELAS, mitochondrial encephalomyopathy/ lactic acidosis/stroke). These disorders may arise from point mutations in or deletions of large segments of mitochondrial DNA. In many cases, the specific enzyme affected is known (e.g. pyruvate dehydrogenase deficiency). Similarly, defective nuclear encoded proteins involved in mitochondrial metabolism or drugs interfering with respiration (e.g., AZT or Adriamycin) can also lead to mitochondrial cytopathies.

Mitochondrial cytopathies can be classified by the site of the defect in mitochondrial oxidation. Defects in substrate transport (e.g. carnitine or carnitine-palmitoyl-transferase deficiencies), substrate metabolism (e.g. deficiencies in pyruvate dehydrogenase, pyruvate carboxylase, fatty acid oxidation, or organic acid metabolism), Krebs cycle activity (e.g. defects in oxoglutarate dehydrogenase or fumarase), the respiratory chain (NADH-Q reductase or cytochrome deficiencies), or energy coupling (ATP synthase defect, mitochondrial uncoupling diseases).

Cumulative alterations in mitochondrial metabolism have been suggested as an underlying cause of diseases associated with aging, including Alzheimer's and diabetes mellitus. Furthermore, mitochondria are the site of initiation of programmed cell death (apoptosis) and probably are the key factor in determining whether or not a cell will recover from an ischemic insult or proceed to necrosis.

Thus, mitochondria are central to the survival and function of the cell under normal conditions and play a major role in adapting to environmental stress.

Thus, it would be desirable to have a method of studying mitochondrial function as well as methods of assessing the effect of different chemicals on mitochondrial function. It would be particularly desirable to identify compounds that selectively modulate mitochondrial function. It would be also useful to detect compounds that affect mitochondrial $K_{ATP}$ channels.

SUMMARY OF THE INVENTION

The present invention relates to methods of assaying for mitochondrial function and more particularly to methods of identifying compounds that selectively modulate mitochondrial function. In one aspect, the present invention relates to methods of detecting compounds that can positively impact mitochondrial function and increase cell energy output. In a related aspect, the invention relates to methods of detecting compounds that can decrease mitochondrial function in diseased cells. The present invention has a variety of useful applications including use in screens to detect compounds that can enhance overall health and fitness.

More particularly, the invention includes methods for detecting the effects of agents acting on mitochondrial metabolism in intact cells by utilizing endogenous redox potential sensitive fluorophores located in the mitochondria. The methods of the invention can enable low cost high throughput screening of compounds which modify the functional state of mitochondria for therapeutic applications. Methods of the invention are applicable to the discovery of agents which modify the activity of any of the steps in energy metabolism. For instance, an exemplary and preferred application detects mitochondrially active agents in intact cardiac cells.

In general, the methods of the present invention are useful for detecting drugs that alter mitochondrial function. For example, in one aspect, the invention provides a drug detection assay by measuring endogenous fluorescence in intact cells. In a normal oxygenated medium, the mitochondrial matrix is significantly reduced. Drugs that decrease the membrane potential across the inner mitochondrial membrane cause oxidation of the matrix, which is detected as a change in endogenous fluorescence by the methods of the present invention. Accordingly, the methods of the present invention are well-suited to detect compounds that can selectively enhance or decrease mitochondrial function.

In the present methods, cells are cultured and illuminated at wavelengths suitable to excite endogenous fluorescence. Preferably the fluorescence is due to changes in the redox state of endogenous molecules located in the mitochondria. These endogenous molecules function as reporters of mitochondrial oxidation state. Preferred molecules include endogenous proteins that comprise fluorescent molecules such as a flavin moiety, or endogenous fluorescent molecules such as NAD.

One aspect of the invention relates to a method for identifying a compound capable of modulating mitochondrial function comprising contacting a eukaryotic cell with one or more candidate compounds and detecting a change in the mitochondrial redox state. Preferably, endogenous fluorescence of the cell mitochondria is indicative of a change of redox state. The change in the redox state is an increase or decrease in the state of the mitochondria oxidation. That change is typically related to a suitable control assay as described below.

In certain preferred methods of the present invention, the fluorescence is measured of a nicotinamide adenine dinucleotide (NAD) or a flavin adenine dinucleotide (FAD) moiety, such as a protein comprising a linked flavin adenine dinucleotide (FAD) moiety. In embodiments comprising such a FAD-linked protein, preferably the FAD-linked protein is linked to a protein component of a mitochondrial redox pathway.

In preferred methods, detection of the mitochondrial redox state further comprises measuring a change in fluorescence of an NAD molecule or FAD-linked enzyme, and correlating that change to a control assay comprising a mitochondrial oxidizing or reducing agent. Illustrative oxidizing agents include dinitrophenol, and illustrative reducing agents include cyanide.

In certain embodiments of the present invention, the cell is contacted with a plurality of candidate compounds or a library of candidate compounds.

In certain embodiments the steps of contacting a eukaryotic cell with one or more compounds and detecting the change in the mitochondrial redox state of the cell are performed a number of times substantially simultaneously. These steps can be performed e.g. in a multi-well plate.

The eukaryotic cell used in certain methods of the present invention comprises a cardiac cell or a precursor cell thereof. In certain preferred embodiments, the eukaryotic cell is a cardiac cell or precursor cell thereof that is immortalized. In other preferred methods, the cardiac cell or precursor cell thereof is a primary cell. The cell may comprise a ventricular myocyte or a skeletal myoblast.

The present invention relates to methods for detecting many different types of drugs capable of modulating mitochondrial function. The present invention also relates to methods wherein the candidate compound activates a mitochbndrial $K_{ATP}$ channel. Further, it relates to methods of assaying the activity of mito$K_{ATP}$ channels using fluorescence methods. In certain preferred embodiments, the compound does not substantially activate a sarcolemmal $K_{ATP}$ channel.

In certain embodiments of the present methods, the cell is contacted with the candidate compound(s) in vitro. In other embodiments, the cell is contacted with the candidate compound(s) in vivo. In yet other embodiments the cell is a tissue and the tissue is treated with the candidate compound ex vivo.

The present invention further relates to a method for detecting a compound capable of modulating mitochondrial redox potential, the method comprising:
  a) providing a population of eukaryotic cells;
  b) contacting a first portion of the cells with one or more candidate compounds;
  c) contacting a second portion of the cells with a known mitochondrial oxidizing or reducing agent; and
  d) measuring a difference between mitochondrial fluorescence produced in steps b) and c).

It will be appreciated that in cases where the mitochondrial fluoresecence of a known oxidizing or reducing agent is known, it will not always be necessary to perform step c), above.

In particular embodiments of this method, the cells are ventricular cells and the method further comprises measuring mitochondrial $K_{ATP}$ ion channel currents in those cells. In some embodiments of this method, the compound activates a mitochondrial $K_{ATP}$ ion channel in the cells. In other embodiments, the method further comprises measuring sarcolemmal $K_{ATP}$ ion channel currents in the cells. In some examples of such methods, the drug does not substantially activate the sarcolemmal $K_{ATP}$ ion channel currents at comparable concentrations.

In certain embodiments of the methods, the mitochondrial fluorescence is activated by a light at a wavelength of from about 250 to about 650 nm. In these embodiments, the step of detecting or measuring is accomplished by fluorescence microscopy.

The methods of the present invention are applicable to nearly any eukaryotic cell. Preferred cells comprise detectable mitochondrial fluorescence. For example, such cells will often include cells from highly energetic tissues such as muscle and particularly cardiac and skeletal muscle cells. In addition certain rapidly dividing cells can also be used such as cancer cells (primary or cultured cell line) and immature cells (e.g., hemapoeitic cells). However, in preferred embodiments, the eukaryotic cells are selected from the group consisting of H9C2 (rat ventricular myocyte-derived cell line), AT-1, HL-1 (atrial tumor derived cell line) and C212 (murine skeletal muscle-derived cell line) cells.

Preferably, the methods identify a candidate compound drug that modulates mitochondrial oxidation (e.g. mitochondrial flavoprotein oxidation) by at least about 10%, 20%, 30%, 40%, 50%, 60%, 70%, 80%, 90% or 100%, in a mitochondrial redox assay of the invention relative to a control (i.e. the same assay where the candidate compound has not been exposed to the test cells). The $EC_{50}$ of identified candidate compounds is preferably no more than about 10 $\mu$M in a standard whole-cell-patch-clamp assay.

The invention further relates to a method of detecting the activity of a mitochondrial ion channel or mitochondrial transporter comprising contacting a eukaryotic cell with one or more candidate compounds and detecting a change in the mitochondrial redox state as indicative of the activity of the ion channel or transporter.

The invention also further relates to drug compounds obtained by the above-described method.

BRIEF DESCRIPTION OF THE DRAWINGS

FIGS. 1(A) and (B) are graphs showing the effect of diazoxide on flavoprotein fluorescence and $I_{K\ ATP}$, respectively.

FIG. 2(A) is a graph showing the effect of 5-HD on the oxidative effect of diazoxide on flavoprotein and FIG. 2(B) is a graph showing effect of 5-HD.

FIGS. 6(A) and (B) show the effect of pinacidil on flavoprotein fluorescence and $I_{KATP}$, respectively.

(Control), after 3 minute exposure to diazoxide (Diazo), after exposure to dinitrophenol (DNP) and cyanide (CN).

Figure 9:
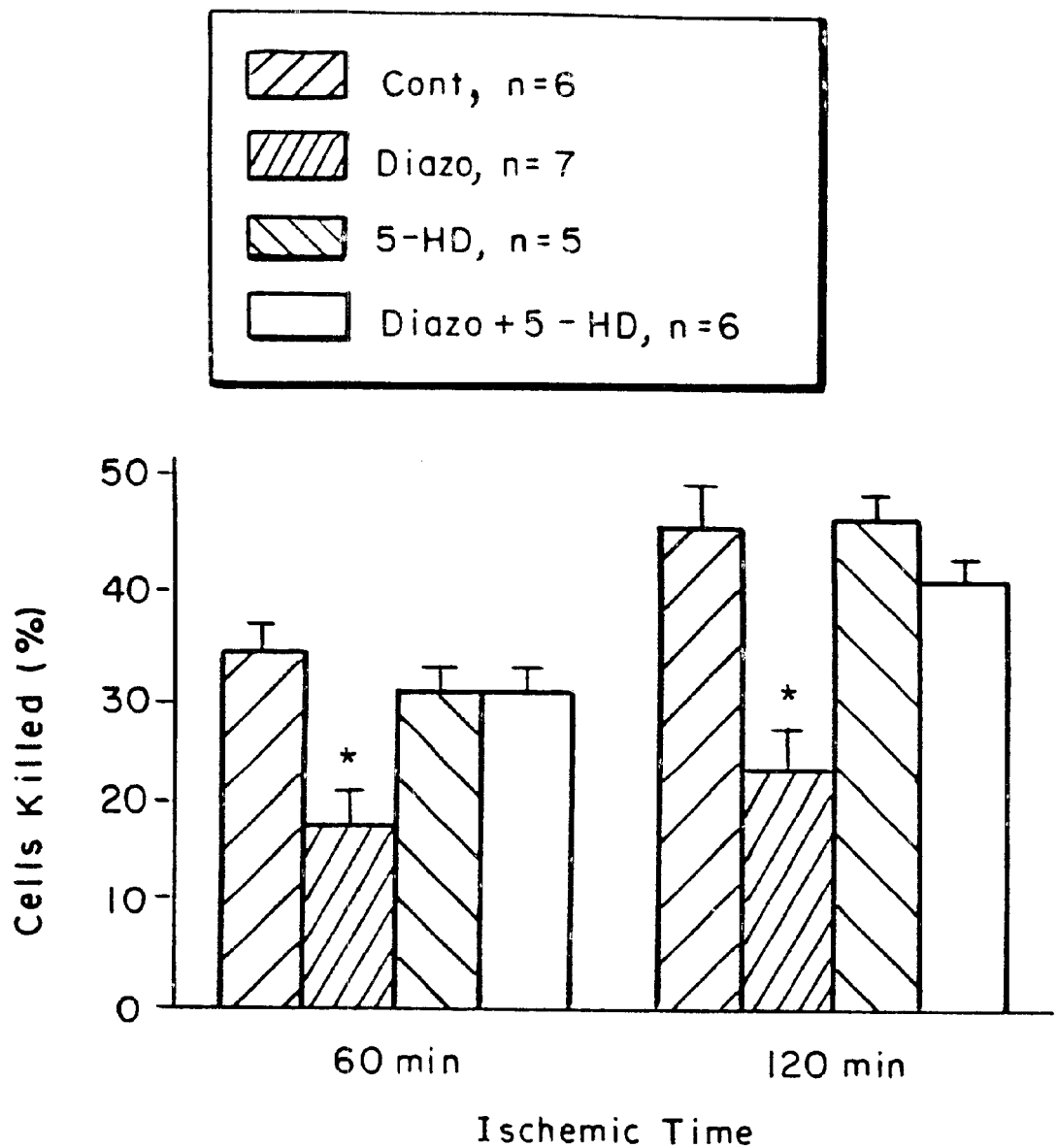

FIG. 9 is a graph of pooled data showing protection of rabbit ventricular myocytes from ischemia by diazoxide.

DETAILED DESCRIPTION OF THE INVENTION

We have found methods of screening compounds that modulate the function of the mitochondria, particularly affecting the redox state of that organelle. As described above, the methods are well-suited to detect compounds capable of modulating mitochondrial function. One method of the present invention for detecting a compound capable of modulating mitochondrial function comprises contacting a eukaryotic cell with one or more candidate compounds and detecting a change in the mitochondrial redox state.

The present methods of identifying compounds that modulate mitochondrial function are more easily performed than previously known methods. Furthermore, the present methods involve minimal cost or expense to perform, as compared to other methods.

The term "candidate compound" as used herein refers to any chemical compound that can be added to a eukaryotic cell, and may comprise a compound that exists naturally within the cell or is exogenous to the cell. The compounds include native compounds or synthetic compounds, and derivatives thereof. These compounds may also be referred to herein as "compound to be tested" or "compounds of interest".

The compounds to be identified modulate the function of mitochondria preferably by eliciting a change in the redox state of the mitochondria. The term "redox state" means the degree or level of oxidation or reduction of the matrix of the mitochondria at any given time. In a normal oxygenated environment, the mitochondrial matrix is substantially in a reduced state. The redox state of the mitochondria can change as the result of many factors. As described above, certain disease states can alter the redox state of the mitochondria. In addition, certain compounds, or drugs, may alter the redox state of the mitochondria. For example, drugs that decrease the membrane potential across the inner mitochondrial membrane cause oxidation of the matrix. For example, the opening of any potassium-selective ion channels in the inner mitochondrial membrane would tend to dissipate the membrane potential established by the proton pump. (see e.g., Garlid, K. D., *Biochimica et Biophysica Acta,* 1996, 1275: 123–126). Such dissipation accelerates electron transfer by the respiratory chain, and leads to net oxidation of the mitochondrial matrix.

Other processes may also change the redox state, e.g., changes in metabolism, glycolysis, oxidative phosphorylation, Kreb cycle, etc. Thus, the mitochondrial redox state is an important indicator of mitochondrial function. Compounds that can affect the degree of mitochondria oxidation are generally referred to herein as "mitochondria modulating compounds" or other similar term.

The detection of the redox state of mitochondria can be accomplished by methods known in the art. Certain components within the mitochondria fluoresce in response to changes in the redox state of the mitochondria. Endogenous fluorescent molecules in the mitochondria comprise nicotinamide adenine dinucleotide (NAD/NADH), or molecules that comprise a flavin adenine dinucleotide (FAD) moiety. The fluorescence of a FAD-containing molecule increases as the oxidation state inside the mitochondria increases, and decreases as the interior becomes reduced. The fluorescence of NAD decreases as the oxidation state inside the mitochondria decreases, and increases as the interior becomes reduced. Thus, the degree of fluorescence, or change in fluorescence, provides a measurement of the redox state of the organelle. (Chance, B., et al., *Am. J. Physiol.,* 1972, 223 :207–218; Hajnoczky, G., et al., *Cell,* 1995, 82: 415–424). Other methods for detecting a change in the mitochondrial redox state of the cell also could be employed.

The eukaryotic cells used in the methods of the present invention are sometimes referred to herein as "test cells" or "cells to be tested."

The steps in the methods of the present invention can be performed in any one of a number of ways. For example, a population of cells to be tested can be divided into portions and the portions placed in the wells of multi-well plates, test tubes or eppendorf tubes, or other such holders as known in the art. Furthermore, the contacting of the cells with one or more candidate compounds can be performed in numerous ways.

In one method for identifying a mitochondrial modulating compound, at least one portion of the cells to be tested are exposed to at least one candidate compound, while another portion of the cells acts as a control, without exposure to any compounds. If desired, another portion of the cells is exposed to a compound that is known to either reduce or oxidize the mitochondria. The numbers of portions of cells to be tested will depend on the number of candidate compounds. The mitochondria redox state of the cells is then measured.

In assays that measure fluorescence of a molecule as an indicator of the redox state of the mitochondria, the cells are exposed to an appropriate wavelength of light, selected to excite the fluorescent molecule. One of ordinary skill in the art can readily select the appropriate wavelength and source of light by known methods in conjunction with the teachings described herein. The amount of fluorescence of the cells exposed to the candidate compound is compared to the fluorescence of the control cells. The difference in fluorescence is correlated to the change in the redox state of the mitochondria produced by exposure of the cells to the candidate compound as compared to the control cells.

In other embodiments, the fluorescence of the test cells is measured prior to addition of one or more of the candidate compounds. In this embodiment, fluorescence is then measured again after the cells are contacted with the candidate compounds. Alternatively, fluorescence is measured during the course of contacting the cells, so that the change in fluorescence can be measured simultaneously with the contact. The change in fluorescence is correlated to a change in the redox state of the mitochondria in response to the candidate compounds.

The cells may be exposed to one or more candidate compounds sequentially. That is, if the cells are divided into portions, each portion of test cells may be contacted with one compound and the fluorescence in response to that compound measured. The cells may then be washed by methods known in the art and then contacted with another candidate compound and fluorescence in response to that compound measured. These washing, contact and measuring steps can be repeated numerous times depending on the number of compounds to be tested. Alternatively, the washing step can be eliminated and the compounds added sequentially.

The cells can be contacted with a library of candidate compounds. For example, the conditions are optimized to provide a measurable and reversible change in fluorescence in response to known compounds, e.g., diazoxide and dinitrophenol (DNP). Then each compound in the library is placed in a well in a multi-well plate containing a portion of cells to be tested. The compounds that produce the desired response, e.g., increase in oxidation, can be selected based upon the degree of fluorescence, e.g., increase in fluorescence produced by the cells.

High-throughput screening involves the testing of a range of different chemical entities in biochemical assays. Any of the methods of identifying mitochondrial modulating compounds described herein can be used for high-throughput screening assays. The "hits", i.e., compounds that produce the desired response, found by any of the methods, can then be further characterized according to methods known in the art, e.g., using cellular physiology and imaging methods.

In other embodiments, after the cells are contacted with candidate compounds, the cells are further exposed to conditions that create or simulate a disease state. For example, to test a compound for cardioprotective properties the cells are exposed to simulated ischemia and cell injury subsequent to treatment with one or more candidate compounds. Such models are known in the art. An exemplary model is further described below and in the examples that follow. In such a method, the degree of prevention of the disease state is determined by comparing the fluorescence of the cells treated with candidate compounds with the fluorescence of untreated, diseased cells. Candidate compounds are selected if they prevent the degree of fluorescence exhibited by the control cells, i.e., the change in redox state caused by the disease.

In another example, the test cells either have a disease state or normal test cells are subjected to conditions that create a disease state. The diseased cells will have a certain degree of fluorescence based on the redox state created by the disease. The cells are then contacted with candidate compounds and the change in fluorescence in response to the compounds is measured. The compounds that reverse the fluorescence, i.e., the redox state of the cells, due to the disease can be selected.

As discussed above, the fluorescent molecule may comprise a protein which has a flavin adenine dinucleotide (FAD), or the fluorescent molecule may comprise nicotinamide adenine dinucleotide (NAD). In embodiments comprising a FAD-linked protein, preferably the FAD-linked protein is an enzyme component of a mitochondrial redox pathway. The wavelength used to excite the fluorescent molecule is preferably within from about 250 nm to about 650 nm, and most preferably at about 488 nm when the fluorescent molecule contains a FAD moiety. When the molecule contains a NAD moiety, the wavelength is suitably within from about 250 to about 450 nm, and more preferably from about 320 to about 400 nm, with about 360 nm being particularly preferred.

Fluorescence can be recorded using presently known methods and technology, e.g., standard or specialty fluorescent plate readers. The fluorescent images can be analyzed by computer using software designed for such imaging, e.g., ImageTool (Univ. of Texas Health Sciences Center, San Antonio). Fluorescence of NAD moiety can be detected according to methods known in the art, particularly those described in O'Rourke, B., et al., *Science,* 1994, Vol. 265, pp. 962–6. Fluorescence can also be detected by methods, such as, but not limited to fluorescent microscopy, photometry, and photographic film.

As described above, the method may comprise measuring fluorescence of an NAD molecule or FAD-linked enzyme as a result of adding a candidate compound of interest and comparing that fluorescence to the fluorescence in a control assay that comprises a known mitochondrial oxidizing or reducing agent. Useful oxidizing or reducing agents are known in the art. Preferred oxidizing agents comprise dinitrophenol (DNP) and diazoxide. DNP is a protonophore which uncouples respiration from ATP synthesis and collapses the mitochondrial potential and induces oxidation in the mitochondria. A preferred reducing agent comprises cyanide. Cyanide inhibits cytochrome oxidase and thus stops electron transfer. Other oxidizing and reducing agents can be readily selected for use in the control in accordance with the present disclosure.

The known mitochondrial oxidizing or reducing agent can be added to the test cells subsequent to addition of the candidate compounds. In such an assay, the candidate compounds may or may not be washed from the test cells, depending on the assay protocol. The compounds, however, need not be washed from the cells for this assay to work. Thus, if desired, one population of cells can be used to test a number of candidate compounds.

Any eukaryotic cell can be used in the identifying methods. Preferably the cell contains numerous mitochondria, and a sufficient number to enable analysis in accordance with the methods of the invention. In preferred embodiment, the cell comprises a cardiac cell or a precursor cell thereof. These cells may be immortalized or a primary cell. Examples of preferred cells comprise a ventricular myocyte or a skeletal myoblast. For high-throughput screening assays, as described below, the cells should be easy to produce and have good survival rates in culture. Such cell lines can readily be selected by one of ordinary skill in the art. Examples of useful cell lines include H9c2 cells, AT-1 cells and C2C12 skeletal myoblasts. The cells preferably will be selected to elicit a measurable and reversible change in fluorescence.

The methods of the present invention enable the identification of many different types of compounds capable of modulating mitochondrial function. For example, compounds that impact energy output generally, e.g., glycolysis, oxidative phosphorylation, Krebs cycle, etc. can be detected by the present methods. Additionally, mitochondrial function is affected by the activity of many different channels and transporters in the mitochondrial membrane, e.g., potassium pumps, transporters and channels, proton pumps and proton channels. Compounds that affect the activity of any of these channels and transporters can be detected by the methods of the present invention.

The methods described herein are useful for identifying compounds that can be used to treat certain diseases and alter mitochondrial states. Compounds that increase mitochondrial respiration or other mitochondrial output can be identified by the present methods by testing compounds for increasing mitochondrial respiration. Such compounds can be used to increase the overall fitness of an animal or improve the condition of a diseased tissue. In addition, compounds that decrease the energy output of the mitochondria and therefore decrease the energy available to cells can be identified by the methods of the present invention. Compounds that decrease mitochondrial respiration or other mitochondrial output are useful to decrease the division and spread of cancer cells. In addition, the present methods can be used to identify compounds that are prophylactic, e.g., to induce or mimic ischemic preconditioning of cardiac muscle.

Preferred drugs used to induce or mimic ischemic preconditioning act by affecting only mito$_{KATP}$ channels. Not wishing to be bound by theory, in ischemic preconditioning it is believed that opening of mitochondrial $K_{ATP}$ channels dissipates the inner mitochondrial membrane potential established by the proton pump. This dissipation accelerates electron transfer by the respiratory chain, and if uncompensated by increased production of electron donors (such as NADH), leads to net oxidation of the mitochondria. The methods of the present invention include the measurement of mitochondrial redox state by recording the fluorescence of FAD-linked enzymes in the mitochondria, to selectively screen for compounds that affect that redox state.

Preferred compounds for use on myocardial cells detected by the methods of the present invention activate a mitochondrial $K_{ATP}$ channel and reversibly oxidize the mitochondrial matrix, without having an effect on sarcolemmal $K_{ATP}$ channels. As shown in Examples which follow, diazoxide is an example of such a compound that can be detected using the present methods. Diazoxide is a commonly used antihypertensive drug which causes dose-dependent mitochondrial oxidation and is cardioprotective. It is believed that diazoxide is an agonist of mito$K_{ATP}$ channels. The simultaneous measurement of flavoprotein fluorescence using the methods of the present invention and sarcolemmal $K_{ATP}$ currents ($I_{KATP}$) in intact rabbit ventricular myocytes, using whole-cell patch clamp, as described in the Examples below, show that diazoxide, a $K_{ATP}$ channel opener, selectively activates mitochondrial $K_{ATP}$ channels. Diazoxide also protects myocytes against simulated ischemia. Thus, the methods of the present invention are useful for screening for compounds that are capable of protecting cells from ischemia.

The methods of the present invention can also be used to detect compounds that block oxidation induced by other chemicals. In such a methods, the candidate compounds are potential oxidation blockers and are added before, during or after addition of compounds that induce oxidation of the mitochondria. For example, using methods of the present invention, it was found that 5-HD, which has been shown to inhibit $K_{ATP}$ channels in sarcolemma (Notsu, T., et al., *J. Pharmacol. Exp. Ther.*, 1992, 260: 702–708), and isolated mitochondria (Garlid, K. D., et al., *Biophy. J.*, 1997, 72: A39 (Abstract)), reversibly blocks the flavoprotein oxidation induced by diazoxide (FIG. 2a). 5-HD is widely used to block ischemic preconditioning and cardioprotection induced by $K_{ATP}$ channel openers. 5-HD is an effective blocker of mitochondrial $K_{ATP}$ channels.

As discussed above, it is believed that ischemic preconditioning is due to activation of mitochondrial $K_{ATP}$ channels. Thus, preferred assays for testing compounds that activate mitochondrial $K_{ATP}$ channels utilize a cellular ischemia model. In this model, cells are centrifuged into a pellet to simulate the restricted extracellular space and reduced oxygen supply during ischemia, sampled at designated time points and stained with a hypotonic (85 mOsm) trypan blue solution to test the osmotic fragility of the membrane. (See Vander Heide, R. S., et al., *J. Mol. Cell Cardiol*, 1990, 22: 165–181). Previous studies have shown that simulated ischemia preconditions myocytes in this model, (Liu, Y., et al., *Basic Res. Cardiol*, 1996, 91:450–457; Armstrong, S., et al., *Cardiovasc. Res.*, 1994, 28: 72–77), and that the underlying mechanisms for the protection are similar to those in intact hearts. (Armstrong, S., et al., *Cardiovasc. Res.*, 1994, 28: 72–77). Drugs such as diazoxide protect rabbit ventricular myocytes to the same extent as preconditioning. Interestingly, a cardioprotective $EC_{25}$ of 11 μM diazoxide has been reported in intact hearts. (Paucek P., et al., *J. Mol. Cell. Cardiol.*, 1997, 29: A199

Figure 5:
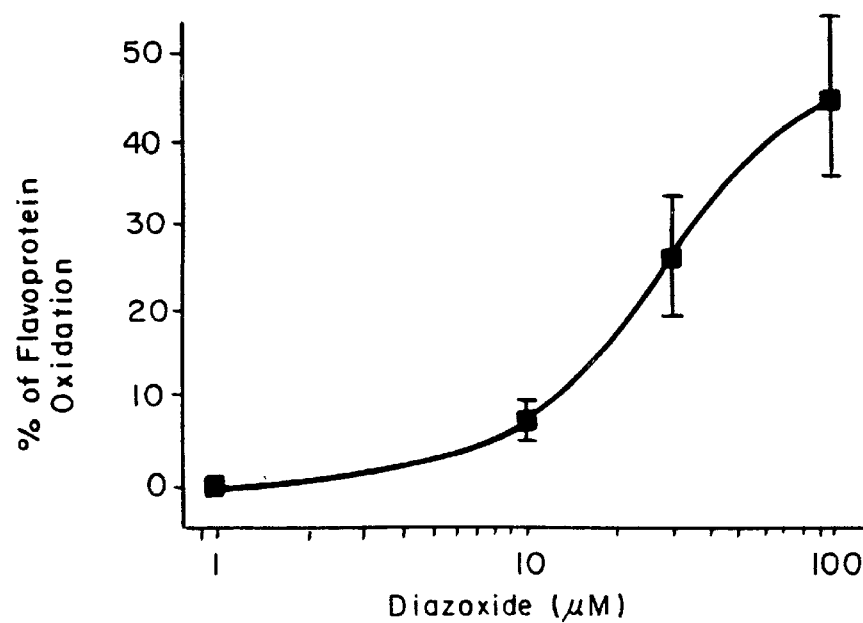
FIG. 5 is a graph showing a dose response curve for diazoxide.
Figure 7A:
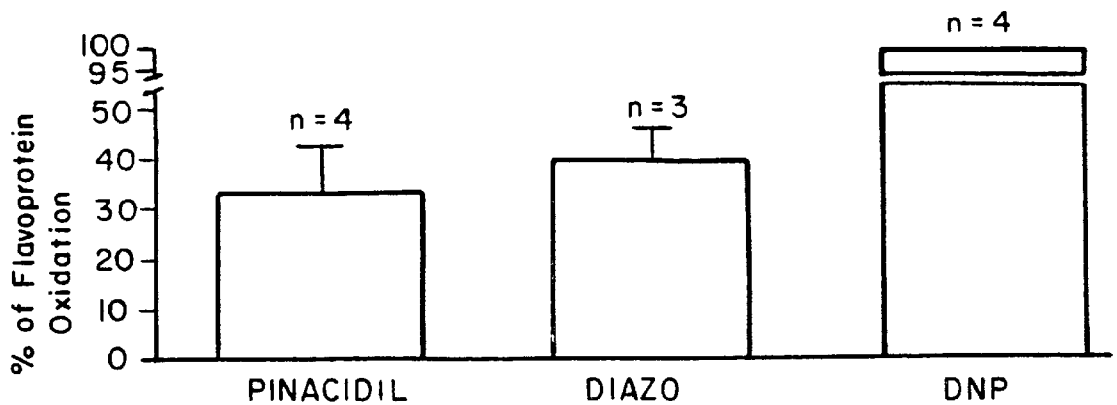
FIGS. 7(A) and (B) are graphs showing summarized data for percentage of flavoprotein oxidation and $I_{KATP}$, respectively.
Figure 7B:
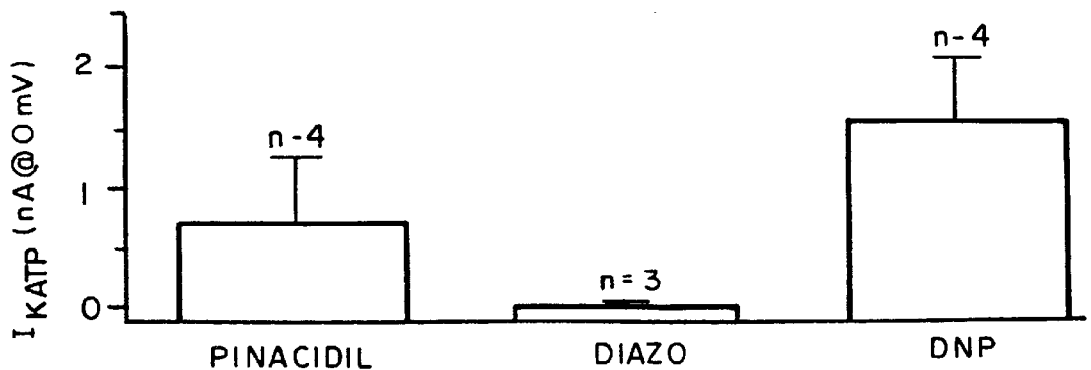

(Abstract)). This concentration corresponds closely to that which was observed to induce flavoprotein oxidation, using the methods of the present invention (FIG. 5).

As also discussed above, it is believed that mitochondrial $K_{ATP}$ channels may serve as effectors of cardioprotection by $K_{ATP}$ channel openers and protect myocytes against ischemic damage. It is theorized that this occurs through the dissipation of mitochondrial membrane potential resulting in a decrease in the driving force for calcium influx through the calcium uniporter. It has been reported that inhibition of the mitochondrial calcium uniporter by ruthenium red protects hearts against ischemia and reperfusion injury, consistent with this hypothesis. (Miyamae, M., et al., *Am. J. Physiol, 1996, 271*: H1245–H2153; Figueredo, V. M., et al., *Cardiovasc Res.* 1991, 25 : 337–342; Park, Y., et al., *J. Pharmacol Exp. Ther.,* 1990, 253: 628–635). Another possibility is that opening of mitochondrial $K_{ATP}$ channels, by decreasing the membrane potential, could promote the binding of the endogenous mitochondrial ATPase inhibitor $IF_1$, and thus conserve ATP during ischemia. (Rouslin, W., *J. Bioenerg. Biomembr.,* 1991, 23: 873–888). Finally, a change of mitochondrial membrane potential could alter glycolytic pathways during ischemia in favor of myocyte survival.

In some embodiments of this methods, the method further comprises measuring mitochondrial $K_{ATP}$ ion channel currents in the cells used in the assay.

As discussed above, preferably the candidate compounds used on cells of myocardial origin do not substantially activate a sarcolemmal $K_{ATP}$ channel. Sarcolemmal $K_{ATP}$ ion channel currents ($I_{KATP}$) can be measured simultaneously with fluorescence in cells, e.g., ventricular cells, by methods known in the art, such as whole cell patch-clamp method, which is generally preferred. See the examples for suitable procedures for this method. References herein to a "standard whole-cell patch assay" are intended to refer to the protcol described in the examples below. Changes in channel currents can be measured in response to the addition of drugs to the cells.

Depending on the intended use of the drug, different effects will be desired. For example, preferred drugs that are to be used to induce cardioprotection do not substantially change the sarcolemmal $K_{ATP}$ ion channel currents. Preferably, compounds identified by the methods of the invention include those that exhibit at least about a 100-fold greater activation of mitochondrial $K_{ATP}$ channels relative to activation of sarcolemmal $K_{ATP}$ channels, more preferably about a 500-fold greater activation of mitochondrial $K_{ATP}$ channels relative to activation of sarcolemmal $K_{ATP}$ channels, still more preferably about a 1000-fold greater activation of mitochondrial $K_{ATP}$ channels relative to activation of sarcolemmal $K_{ATP}$ channels.

As described above, an example of a use of this assay includes the identification of compounds that induce or mimic ischemic preconditioning by increasing oxidation of the mitochondria. Thus, preferably the methods of the present invention identify that increase mitochondrial oxidation.

As discussed above, the methods of the present invention can be used to identify compounds that affect, e.g., the numerous transporters and channels in mitochondria. While the methods have been described above with particular attention to mitochondrial $K_{ATP}$ channels, the methods can be applied to any channel or transporter. For example, to identify compounds that affect proton channels, resulting in a change in the redox state of the mitochondria, the candidate compounds are contacted with the test cells as described above. If the candidate compound changes the redox state of the mitochondria, such change will be detected, e.g., by a change in fluorescence, and a mitochondrial modulating compound will be identified. The effect of these compounds on the redox state can be measured simultaneously with the effect of the compounds on the activity of other channels or transporters through the use of methods described herein, e.g., whole-cell patch clamp.

The compounds identified by the methods of the present invention are useful as additions to enhance cell vitality in cell culture and in vitro assays.

In certain embodiment of the present invention, the test cells comprise cells in a tissue of interest. In such a method, the tissue of interest is treated with the one or more candidate compounds ex vivo. In this embodiment, the tissue of interest or cells from the tissue (sometimes known as primary cells), is removed from a host organism. The cells are then used in the methods described above. That is, the cells are contacted with one or more candidate compounds and the change in the mitochondria redox state of those cells is detected. Subsequently, the treated cells, i.e., oxidized cells, can be implanted back into the recipient host organism.

In certain embodiments, the candidate compounds are contacted to the test cells in vivo. The in vivo assays of the invention are particularly useful for subsequent evaluation of mitochondrial modulating compounds exhibiting suitable activity in an in vitro assay. For example, an animal model of cardiac muscle damage accompanying ischemia or an invasive surgical procedure such as balloon angioplasty is useful. One suitable protocol involves administering to the animal a suitable vehicle or vehicle combined with one or more mitochondrial modulating compounds of interest. The amount of the mitochondrial modulating compound administered will vary depending on several parameters including the extent of damage associated with the ischemia or surgical procedure of interest. In instances where balloon angioplasty is employed, the animal will typically receive a candidate compound in a dose (e.g., i.m. or i.p.) of between about 0.5 to 100, preferably 1 to 20 and more preferably about 10 mg/kg body weight of the animal. A preferred dosage schedule provides for administration of the compound starting 24 hours prior to conducting an invasive surgical procedure or inducing ischemia. Daily injections, e.g., i.m. or i.p., of the compound are generally preferred. Subsequently, the animals are euthanized and the organ, e.g., heart removed for examination.

The term "invasive surgical procedure" means a medical or veterinary technique associated with significant damage to an organ such as the heart, liver or the kidney, or a limb. The invasive surgical procedure can be associated with techniques involving, e.g., cardiac surgery, abdominothoracic surgery, arterial surgery, deployment of an implementation (e.g., a vascular stent or catheter), or endaterectromy. Preferably, the invasive surgical procedure is performed on a mammal such as a primate, particularly a human, rodent or a rabbit, or a domesticated animal such as a pig, dog or a cat. Ischemia can be induced in the animal by methods known in the art.

In other embodiments, the compound is administered to the animal either as a sole active agent or in combination with other active compounds (e.g., 5-HD), or other candidate compounds to be tested. In most embodiments, activity of the candidate compound in a given in vivo assay is compared to a suitable control (e.g., a sham-operated animal) in which the assay is conducted the same as the test assay but without administering the compound to the test subject. A variety of test subjects can be employed, particularly mammals such as rabbits, primates, various rodents and the like.

As noted above, the assays (either in vitro or in vivo) can be conducted in a wide variety of cells, tissues and organs. The assays can detect useful mitochondrial modulating compounds by measuring the redox state of the mitochondria in several cell, tissue and organ settings.

The present invention further provides in vitro kits for detecting compounds capable of modulating mitochondrial function.

The invention also includes diagnostic kit formulations. Kits of the invention preferably include test cells and medium for use in the assay in an immediately usable or readily reconstituted form and preferably any other reagents necessary to ensure the activity and/or growth of the cells. Optionally, the kit includes a known mitochondrial oxidizing or reducing agent. Also optionally, the kit further contains a detection device to facilitate determination of whether the candidate compound is a modulating compound. Also, the kit optionally contains multi-well plates or test tubes for running the assay.

More particularly, in certain preferred kits of the invention, the kit includes a vial or vessel containing test cells and an ampule or vial containing growth medium to sustain the test cells. Such a kit may also include photographic film or other detection device. In use, the test cells are mixed with the growth medium and the candidate compounds are added. After a predetermined period of time, an aliquot of the assay mixture is spotted on or placed near the film, and the film is developed. The degree of spotting on the film indicates the redox state of the cells. Preferably a control, containing the test cells and growth medium, but not the candidate compound, is run simultaneously. For example, if the candidate compound increases the oxidative state of the mitochondria, the film containing the cells contacted with the candidate sample will have a larger and/or darker spot than the control. If the candidate compound decreases the oxidative state, the control film will have a larger and/or darker spot than the cells treated with the candidate compound. The difference in the spotting on the film for the mixture containing the candidate compound and the control is indicative of a change in the redox state of the cells in response to the candidate compound.

All documents mentioned herein are incorporated herein by reference in their entirety.

The present invention is further illustrated by the following examples, which are provided to aid in the understanding of the invention and are not construed as a limitation thereof.

General Comments of Examples

The following examples were performed according to with *The Guide for the Care and Use of Laboratory Animals* published by the US National Institutes of Health (NIH Publication No. 85-23, revised 1985).

Chemicals

In the following Examples, Collagenase (type II) was purchased from Worthington. Diazoxide was obtained from Sigma Chemical Co. Pinacidil and 5-hydroxydecanoic acid sodium (5HD) were purchased from Research Biochemical Int. Tetramethylrhodamine ethyl ester (TMRE) was obtained from Molecular Probes. Diazoxide, pinacidil and TMRE were dissolved in DMSO before added into experimental solutions. The final concentration of DMSO was less than 0.1%.

Electrophysiology and Flavoprotein Fluorescence Measurement

In the following Examples, ventricular myocytes were isolated from adult rabbit hearts by conventional enzymatic dissociation, according to Liu, Y., et al., "Synergistic modulation of ATP-sensitive $K^+$ currents by protein kinase C and adenosine: implications for ischemic preconditioning", *Circ. Res.*, 1996, 78: 443–454, then washed several times with calcium-free solution. Calcium concentration was gradually brought back to 1 mM. Cells were then cultured on laminin-coated coverslips in M199 culture medium with 5% fetal bovine serum at 37° C. Experiments were performed over the next two days.

For whole-cell patch recordings, the internal pipette solution contained (in mM): 120 K-glutamate, 25 KCl, 0.5 $MgCl_2$, 10 K-EGTA, 10 HEPES and 1 MgATP (pH 7.2 with KOH). The external solution included (in mM): 140 NaCl, 5 KCl, 1 $CaCl_2$, 1 $MgCl_2$, and 10 HEPES (pH 7.4 with NaOH). Whole-cell currents were elicited every 6 sec from a holding potential of −80 mV by two consecutive steps to −40 mV (for 100 msec) and 0 mV (for 380 msec). Currents at 0 mV were measured 200 msec into the pulse. Endogenous flavoprotein fluorescence was excited using a xenon arc lamp with a bandpass filter centered at 480 nm, but only during the 100 msec step to −40 mV t to minimize photobleaching. Emitted fluorescence was recorded at 530 nm by a photomultiplier tube and digitized (Digidata 1200, Axon Instruments). (See Paucek, P., et al., "Cardioprotective effect of diazoxide and its interaction with mitochondrial $K_{ATP}$: possible mechanism of cardioprotection", *J. Mol Cell Cardiol*, 1997, 29: A199(Abstract)). Relative fluorescence was averaged during the excitation window and calibrated using the values after dinitrophenol (DNP) and sodium cyanide (CN) exposure.

In some cells, contracture occurred before the fully reduced level (after CN exposure) could be determined. In these cells, data were expressed as a percentage of the DNP-induced fluorescence, since the basal redox state was nearly fully reduced (average 5% oxidation, n=5).

Flavoproteinfluorescence and Mitochondrial Imaging

In the following Examples, Confocal images were obtained using a Diaphot 300 inverted fluorescence microscope with a PCM-2000 confocal scanning attachment (Nikon, Inc.). Fluorescence was excited by the 488 nm line of an argon laser and the emission at 505–535 nm was recorded. A time series of images was collected at intervals of ~10 sec and baseline, diazoxide, DNP and CN images were enhanced by averaging 8–10 sequential images having stable mean fluorescence intensities during the exposure to each agent.

To localize mitochondria, cells were loaded with 100 nM TMRE, which distributes into negatively charged cellular compartments, for 10 min., (Lemasters, J. J., et al., "Measurement of electrical potential, pH, and free calcium ion concentration in mitochondria of living cells by laser scanning confocal microscopy", in *Anonymous: Methods in Enzymology.*, New York, Academic Press, 1995, pp 429–417). TMRE fluorescence was excited with the 535 nm line of a helium neon laser and recorded at greater than 605 nm. A pseudocolor palette was applied to visualize the relative increase in mitochondrial flavoprotein oxidation state.

Images were analyzed on a personal computer using the software program ImageTool (University of Texas Health Sciences Center in San Antonio). All the recordings were performed at room temperature (21–22° C.).

Simulated Ischemia and Cellular Injury

In the following Examples, the procedure to determine cell injury was modified from Vander Heide, et al. Vander Heide, R. S., et al., "An in vitro model of myocardial ischemia utilizing isolated adult rat myocytes", *J. Mol. Cell Cardiol*, 1990, 22: 165–181. After cell isolation, cells were washed with incubation buffer (in mM): NaCl 119, NaHCO$_3$ 25, KH2PO$_4$ 1.2, KCl 4.8, MgSO$_4$ 1.2, HEPES 10, glucose 11, and supplemented with creatine, taurine and amino acids (pH 7.4). Calcium was added into the buffer stepwise (0.25 mM every 5 minutes) to a final concentration of 1 mM. An aliquot of each cell suspension (0.5 ml) was placed in a 0.5 ml microcentrifuge tube and centrifuged for 20 seconds into a pellet. Each pellet occupied a volume of about 0.2 ml. Approximately 0.25 ml of excess supernatant was removed to leave a thin fluid layer above the pellet, and 0.2 ml of mineral oil was layered on the top of the pellet to exclude gaseous diffusion. After 60 min and 120 min of pelleting, 5 µl of cell pellet were sampled through the oil layer and mixed with 75 µl of 85 mOsm hypotonic staining solution (in mM): NaHCO$_3$ 11.9, KH$_2$PO$_4$ 0.4, KCl 2.7, MgSO$_4$ 0.8, CaCl$_2$ 1 and 0.5% glutaraldehyde, 0.5% trypan blue.

Microscopic examination was performed 2–5 min after mixing to determine the permeability of the cells to trypan blue. Cells permeable to trypan blue were counted as dead and expressed as a percentage of the total cells counted (>200 for each sample).

The killing of cells by ischemia was quantified as percentage of the vital cells at the beginning of each experiment (78–90% of total, mean=82±1% n=24). The small percentage of cells (~18%) that were non-viable at the beginning of the experiment were mostly rounded and had been damaged as a known consequence of the enzymatic isolation process. Mitra, R., et al., "A uniform enzymatic method for dissociation of myocytes from hearts and stomachs of vertebrates", *Am. J. Physiol*, 1985, 249: H1056–H1060.

EXAMPLE 1

Individual experiments in each of four groups were performed on cells isolated from different hearts. In the control group (Cont), cells were pelleted and sampled at the 60 min and 120 min. For the diazoxide-treated group (Diazo), 50 µM of diazoxide was added into the solution 15 min before the pelleting. In the third group (5-HD), 100 µM of 5-HD was added into the cell suspension 20 min prior to pelleting. Cells in the Diazo+5HD group were treated the same as in the third group except that 50 µM of diazoxide was added into the cell suspension 15 min before pelleting. Once applied, drugs were not washed out, and thus were present throughout the period of simulated ischemia.

Data are presented in the Figures as means±SEM, and the number of cells or experiments is shown as n. Analysis of variance (ANOVA) combined with Tukey's HSD post-hoc test was used to test for differences among groups for electrophysiological and fluorescence data. Cell pelleting data were analyzed by two-way ANOVA combined with Tukey's HSD post-hoc test. p<0.05 was considered significant.

FIG. 1 shows results from simultaneous measurements of flavoprotein fluorescence and membrane $I_{KATP}$ in cells exposed to diazoxide. The periods of drug treatment are marked with horizontal bars. Diazoxide (100 µM) induced reversible oxidation of the flavoproteins (FIG. 1A) but did not activate $I_{KATP}$ (FIG. 1B).

The redox signal was calibrated by exposing the cells to DNP followed by CN at the end of the experiments. DNP, induced maximal oxidation, while CN caused complete reduction of the flavoproteins (FIG. 1A and FIG. 2A). Although membrane currents were unchanged by diazoxide, $I_{KATP}$ eventually turned on after prolonged exposure to DNP (FIGS. 1B and 2B), indicating that these channels are operable under these experimental conditions despite the inability of diazoxide to open them.

Figure 3:
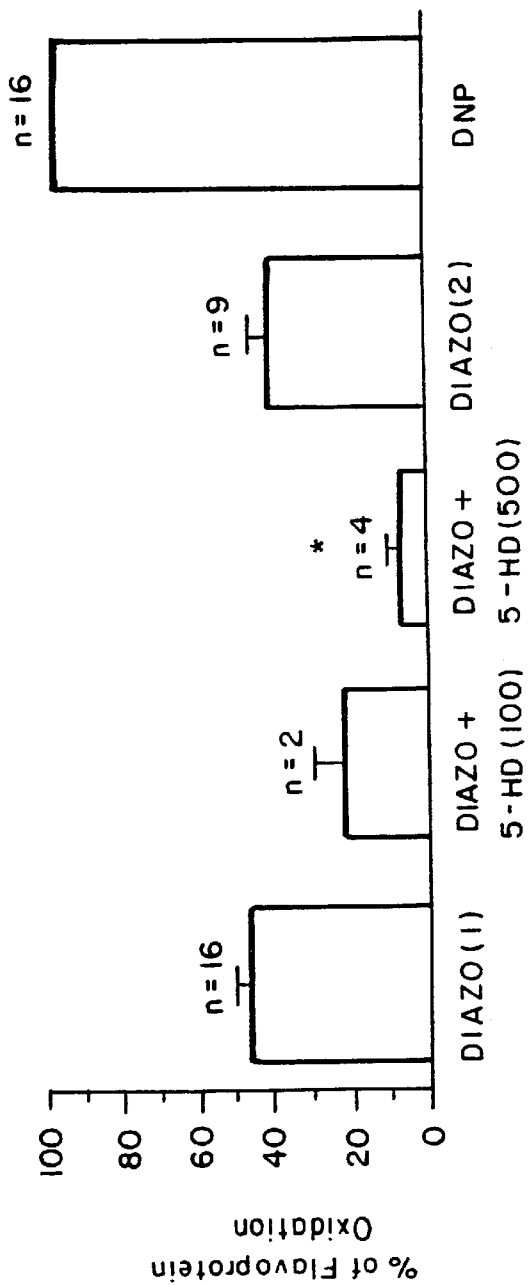
FIG. 3 is a graph showing pooled data for fluorescence.

Diazoxide (100 µM, DIAZO(1)) reversibly increased mitochondrial oxidation to 48±3% of the DNP value (FIG. 3). FIG. 3 shows DIAZO(1), first exposure to diazoxide; DIAZO+5-HD(100), diazoxide in the presence of 100 µM 5-HD; DIAZO+5-HD(500), diazoxide in the presence of 500 µM 5-MD and DIAZO(2), second exposure to diazoxide. DNP, exposure to dinitrophenol. The bar indicates the periods when cells were exposed to drug. The results show that this oxidation was reproducible, because after washout of the response a second exposure to diazoxide (DIAZO(2)) in the same cells increased flavoprotein oxidation to 43±5%. 5-HD (100 µM) attenuated the oxidative effect of diazoxide by about half (DIAZ0+5HD(100)), while 500 µM 5-HD further reduced oxidation to 8±3% (DIAZ0+5-HD(500); p<0.01 vs. DIAZO(1), DIAZ0(2) and DIAZ0+5-HD(100) groups).

Figure 4:
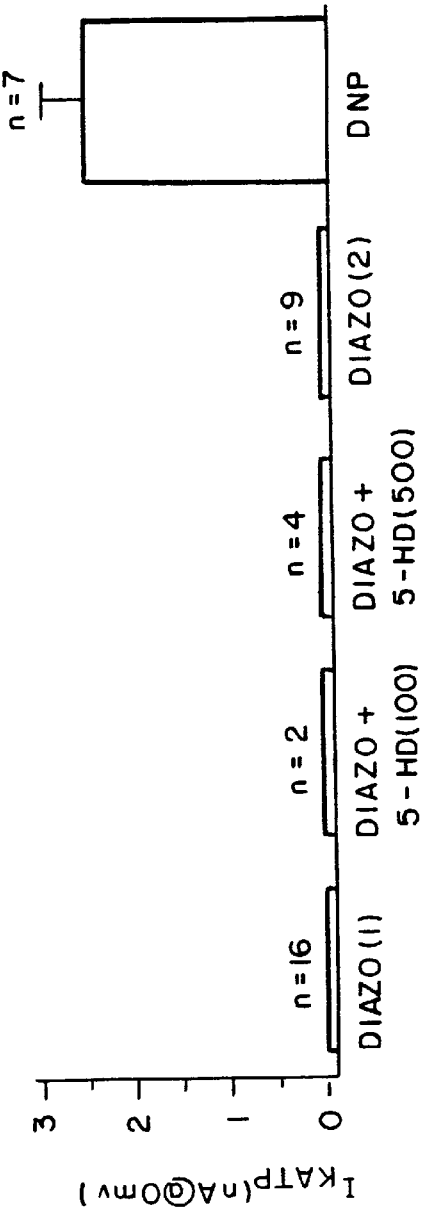
FIG. 4 shows pooled data for $I_{KATP}$.

Treatment with diazoxide and 5-HD did not activate $I_{KATP}$, while prolonged exposure (>6 min) to DNP did turn on $I_{KATP}$ (FIG. 4). In FIG. 4, DIAZO(1) is the first exposure to diazoxide, DIAZ0+5-HD(100) means diazoxide in the presence of 100 µM 5-HD, DIAZO+5-HD(500) means diazoxide in the presence of 500 µM 5-MD and DIAZ0(2) means second exposure to diazoxide. DNP indicates exposure to dinitrophenol. The bar indicates the periods when cells were exposed to drug.

The EC$_{50}$ for diazoxide to induce mitochondrial oxidation is 27 µM, as shown in FIG. 5. Each point in FIG. 5 constitutes measurements from 5–6 cells. *=p<0.01 vs. DIAZ0(1), DIAZ0(2) and DNP groups.

EXAMPLE 2

Effect of Pinacidil on Redox State

Another $K_{ATP}$ opener, pinacidil, which opens sarcolemmal $K_{ATP}$ channels and is known to induce pharmacological preconditioning. Critz, S., et al., "Pinacidil but not nicorandil opens ATP sensitive K$^+$ channels and protects against simulated ischemia in rabbit myocytes", *J. Mol Cell Cardiol*, 1997, 29: 1123–1130.

As shown in FIG. 6A, pinacidil (100 µM) induced 35±8% mitochondrial oxidation, comparable to the effect of diazoxide exposure in the same cell (41±5%). Unlike diazoxide, pinacidil activated sarcolemnal $I_{KATP}$ (0.74±0.54 nA measured at 0 mV) in addition to inducing flavoprotein oxidation, (FIG. 6B) suggesting that pinacidil activates both mitochondrial and sarcolemmal $K_{ATP}$ channels.

EXAMPLE 3

Figure 8A:
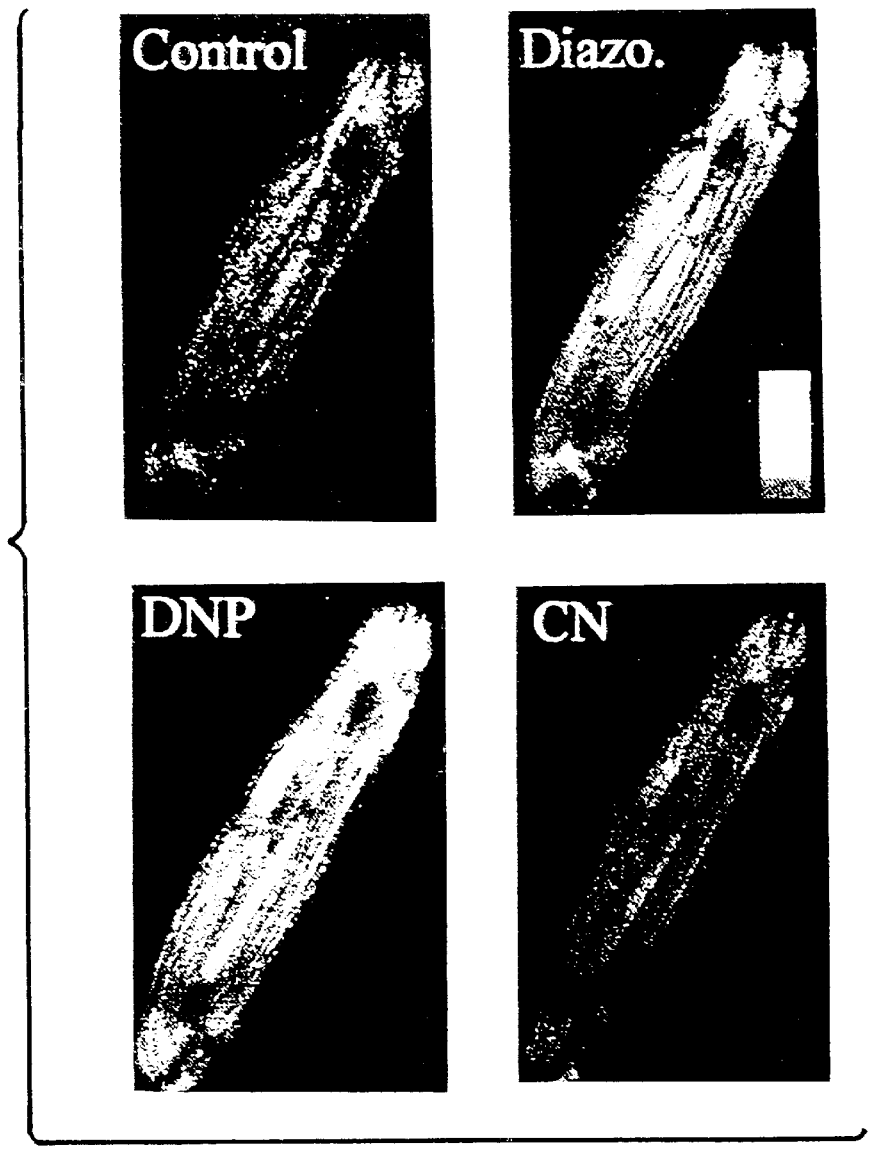
FIG. 8 are confocal images showing (A) a cell at baseline and (B) a cell after TMRE loading of the same cell.
Figure 8B:
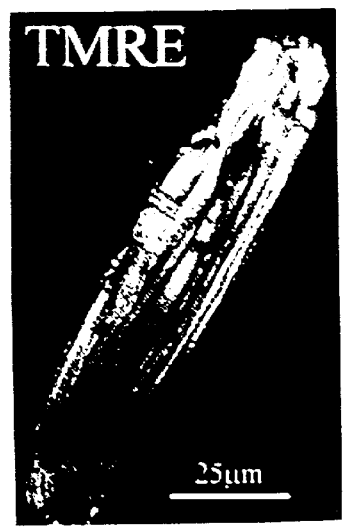

The subcellular site of diazoxide action was localized by imaging flavoprotein fluorescence (FIG. 8). Fluorescence is low under control conditions (Control), but exposure to diazoxide (Diazo) increased fluorescence in strips parallel to the myofibril orientation. Subsequent exposure to DNP increased fluorescence even further (DNP), in a pattern similar to that revealed by diazoxide. CN reduced the fluorescence to the basal level (CN). The distribution of fluorescence induced by diazoxide and DNP is as expected for mitochondria, which occupy ~35% of cardiomyocyte volume and are clustered longitudinally between myofibrils.

Sommer, J. R., et al., "Ultrastructure of cardiac muscle, in Berne RM (ed)", *Handhook of Physiology. Section 2. The Cardiovascular System*. Bethesda, Md., Am. Physiol Soc, 1979, pp 113–186.

This correspondence was further confirmed by using TMRE (old FIG. 3B), which distributes into negatively charged cellular compartments, to localize mitochondria. Lemasters, J. J., et al., "Measurement of electrical potential, pH, and free calcium ion concentration in mitochondria of living cells by laser scanning confocal microscopy, in Anonymous: *Methods in Enzymology*. New York, Academic Press, 1995, pp 429–417. The pattern of TMRE fluorescence was virtually identical to that of the flavoprotein fluorescence induced by diazoxide.

EXAMPLE 4

FIG. 9 shows the fraction of cells killed by 60 or 120 min of ischemia as a percentage of the total number of viable cells prior to ischemia. Cell killed (%) was calculated as number of cells killed by ischemia as a percentage of the total viable cells prior to ischemia. In that FIG. 9, the following designations have the following meanings: Cont, control. Diazo, 50 $\mu$M diazoxide. 5-HD, 100 $\mu$M 5-HD. Diazo+5-HD, diazoxide in the presence of 5-HD. *=p<0.01 vs. the other three groups. 60 min and 120 min killed 35±2% and 46±4% of cells respectively in the control (Cont). However, inclusion of 50 ±M diazoxide significantly decreased cell death during simulated ischemia to about half of that in the controls (18±3% after 60 min, and 23±4% after 120 min, p<0.01 vs. Cont). The protection by diazoxide was completely blocked by 100 $\mu$M 5-HD (31±2% after 60 min and 47±2% after 120 min). 5-HD alone did not significantly alter the percentage of cells killed by simulated ischemia: 31±2% after 60 min and 47±2% after 120 min. Glybenclamide (1 $\mu$M) also blocked the protection from diazoxide (data not shown). Diazoxide at 100 $\mu$M had a similar protective effect (data not shown).

For each experiment, there was always an isochronal nonischemic group in which cells were not pelleted. In these groups, less than 5% of trypan-blue-resistant cells became permeable to trypan blue during the 2-hour experiments.

The invention has been described in detail with particular reference to the preferred embodiments thereof. However, it will be appreciated that modifications and improvements within the spirit and teachings of the inventions may be made by those in the art upon considering the present disclosure.

What is claimed is:

1. A method for identifying a compound capable of increasing or decreasing the redox state of mitochondria, comprising:

(a) contacting a eukaryotic cell with one or more candidate compounds, and (b) measuring fluorescence of an endogenous mitochondrial component;

(c) detecting a change in fluorescence upon contact with a candidate compound, wherein a change in fluorescence is indicative of an increase or decrease in the mitochondrial redox state of the cell; and (d) selecting a compound or compounds which causes a change in fluorescence, wherein the candidate compound activates a mitochondrial $K_{ATP}$ channel.

2. The method of claim 1 wherein the candidate compound does not substantially activate a sarcolemmal $K_{ATP}$ channel.

3. A method for identifying a compound capable of increasing or decreasing the redox state of mitochondria, comprising.

(c) contacting a eukaryotic cell with one or more candidate compounds, and (b) measuring fluorescence of an endogenous mitochondrial component;

(c) detecting a change in fluorescence upon contact with a candidate compound, wherein a change in fluorescence is indicative of an increase or decrease in the mitochondrial redox state of the cell; and (d) selecting a compound or compounds which causes a change in fluorescence;

wherein the oxidation state of the endogenous mitochondrial flavin moiety is monitored by fluorescence, and an increase in fluorescence indicates a increased oxidation state and a reduced fluorescence indicates an reduced oxidations.

* * * * *